United States Patent
Rhodes et al.

[11] Patent Number: 5,425,272
[45] Date of Patent: Jun. 20, 1995

[54] RELATIVE RESONANT FREQUENCY SHIFTS TO DETECT CRACKS

[75] Inventors: George W. Rhodes; James Schwarz, both of Albuquerque, N. Mex.

[73] Assignee: Quatro Corporation, Albuquerque, N. Mex.

[21] Appl. No.: 159,142

[22] Filed: Nov. 30, 1993

[51] Int. Cl.[6] .................... G01H 13/00; G01N 29/12
[52] U.S. Cl. .......................................... 73/579; 73/646
[58] Field of Search ................ 73/579, 12.01, 646

[56] References Cited

U.S. PATENT DOCUMENTS

| | | | |
|---|---|---|---|
| 4,283,952 | 8/1981 | Newman | 73/579 |
| 4,829,823 | 5/1989 | Michel | 73/579 |
| 5,062,296 | 11/1991 | Migliori | 73/579 |
| 5,257,544 | 11/1993 | Khuri-Yakub et al. | 73/579 |
| 5,285,687 | 2/1994 | Ringel et al. | 73/579 |

*Primary Examiner*—Hezrone E. Williams
*Assistant Examiner*—Rose M. Finley
*Attorney, Agent, or Firm*—Ronald R. Snider

[57] ABSTRACT

An ultrasonic measurement method for distinguishing between unflawed and flawed parts comprises the steps of detecting at least two prominent resonant response frequencies, measuring the frequency difference between the two frequencies, determining the ratio of the frequency difference to one of said frequencies, and comparing the ratio to a predetermined part criterion. Resonant response frequencies dependant upon physical characteristics such as dimensions and weight are compared to other resonances which are at frequencies dependant upon stiffness of the part.

18 Claims, 6 Drawing Sheets

RELATIVE RESONANT FREQUENCY SHIFTS TO DETECT CRACKS

BACKGROUND OF THE INVENTION

1. Field of the Invention

This invention relates in general to an ultrasonic testing device and, more particularly, to the use of a plurality of piezoelectric sensors or transducer receiver assemblies in an ultrasonic resonant spectrometer to measure the ultrasonic characteristics of objects for use in testing for the presence of imperfections in vibrated objects. The plurality of measurements are compared to form a unique signature at a given set of frequencies.

This invention relates to investigation of specific resonant responses and a method of qualifying parts as good or bad.

2. The Prior Art

It has long been attempted to test objects for imperfections by utilizing the natural resonance of the objects when vibrated. Particularly when the objects to be tested are mass produced, such as ball bearings, where it is important to meet safety standards.

Recent efforts have been directed to measuring objects of known shape and frequency. See U.S. Pat. No. 4,976,148, incorporated herein by reference.

U.S. Pat. No. 4,858,469 shows two receiver transducers used for analysis of vibrations of timbers in response to vibrations and impact. Surface and shear vibrations are detected by detection of the first half cycle of timber vibration. The first half cycle is not a resonant response measurement and is the first response to an impact.

U.S. Pat. Nos. 4,758,964, to Bittner 4,577,500, to Mishiro 4,603,585, to Atalay 4,212,205, to West 4,858,469 to Hosgood and 4,166,393 to Lindner are examples of vibration (or resonance) measurement with more than one vibration sensor.

It is an object of the present invention to provide a reliable and cost effective means for testing objects of various shapes and at numerous frequencies in order to detect imperfections.

Additional objects, advantages and novel features of the invention will be set forth in part in the description which follows, and in part will become apparent to those skilled in the art upon examination of the following, or may be learned by practice of the invention.

SUMMARY OF THE INVENTION

This invention provides for improved detection of flawed and unflawed parts from a production run. In this method, at least two prominent resonant frequencies of a part are sensed, and the frequency difference between the two prominent resonant frequencies is measured. Next, the ratio of the frequency difference to one of said prominent resonant frequencies is determined, and compared to a predetermined part criterion. The ratio may also be determined by dividing by any other number which is consistent from sample to sample such as the average of the two resonant frequencies.

The resonant frequency may be at frequencies which are dependant upon dimensions of the part and dependant upon the stiffness of the part. When a first resonant frequency is dependant upon dimensions and a second resonant is dependant upon stiffness of the part, the change in the difference in frequency observed between good and bad parts can be used to distinguish between good and bad parts. According to this invention, resonant frequency dependant upon dimensions will shift very little, while the resonant frequency dependant upon stiffness will shift a relatively large amount when the part has a crack.

This invention provides for measurement of vibration of a test object by two or more measurement transducers and recording of the transducer output amplitudes at a plurality of test frequencies.

Each output transducer is connected to a receiver which provides an output at a fixed frequency and at an amplitude proportional to the vibration detected by the sensing transducer.

In the method of this invention, acoustic waves having frequencies swept over a predetermined frequency range are applied to an object. The response of the object to the acoustic waves at a plurality of sensor locations is detected. The frequency of at least one resonant response within the frequency range of each of the plurality of locations is then determined, and excitation frequency and response to the excitation frequency is recorded. Recording may be of at least one resonant response (the frequency of at least one resonant response and its magnitude).

In this apparatus and method, the resonant response may comprise an amplitude measurement as a function of frequency. Further, the resonant response may also be performed when the tested part is dry or wet. Wetting of the part may fill cracks and with some suitable liquid such as isopropanol, thereby producing a different response in the dry and wet measurements only if cracks are present.

To achieve the foregoing and other objects, and in accordance with the object of the present invention, as embodied and described herein, the apparatus of the present invention uses an ultrasonic excitation transducer and a plurality of ultrasonic detectors. The excitation transducer assembly contacts and vibrates the sample over an operative frequency range; and a plurality of receive transducer assemblies contact the sample and produce outputs which are sent as separate signals to a processor. The receive transducer assemblies derive output responses from the samples, and the excitation or drive transducer assembly excites the sample over a resonant response frequency range.

The terms resonance and resonant response, as used in this application, refer to the total response which can be described as the frequency, the width in frequency and the amplitude.

Excitation may include a series of step increases in frequency and at intervals in frequency much less than the width of the resonance and at intervals in time much less than the time required for the resonance to decay after excitation at a fixed frequency.

The receive and drive transducer assemblies may consist of the same or similar configurations, and may be any device that produces an electrical output at the frequency of vibration of the sample which is proportional to the amplitude of the vibrations in the sample. Each output signal is connected to the input of a suitable receiver that amplifies and removes noise from the signal. Output response signals (natural resonance response data) can be used to establish a standard when testing objects of the same shape. Objects known to be free of imperfections and/or of acceptable minimum imperfections can be vibrated over a specific frequency range to obtain a spectrum of resonant responses.

For large, complex or expensive objects which do not have a known intrinsic acoustic resonance, it is not economically possible to establish a standard spectrum of resonant response or rejection limits. However, an object can be tested when manufactured and again after use, to screen for imperfections occurring during use. Imperfections can be caused by external forces on the object such as minor vibrations from traffic or seismic activity, wind vibration, mechanical vibration, and other pressures exerted during use. Under these conditions, the ultrasonic testing device consists of a drive transducer, a plurality of receive transducers, a receiver, and a data collection device.

BRIEF DESCRIPTION OF THE DRAWINGS

The accompanying drawings illustrate an embodiment of the present invention and together with the description, serves to explain the principles of the invention.

DETAILED DESCRIPTION OF THE INVENTION

Figure 1:
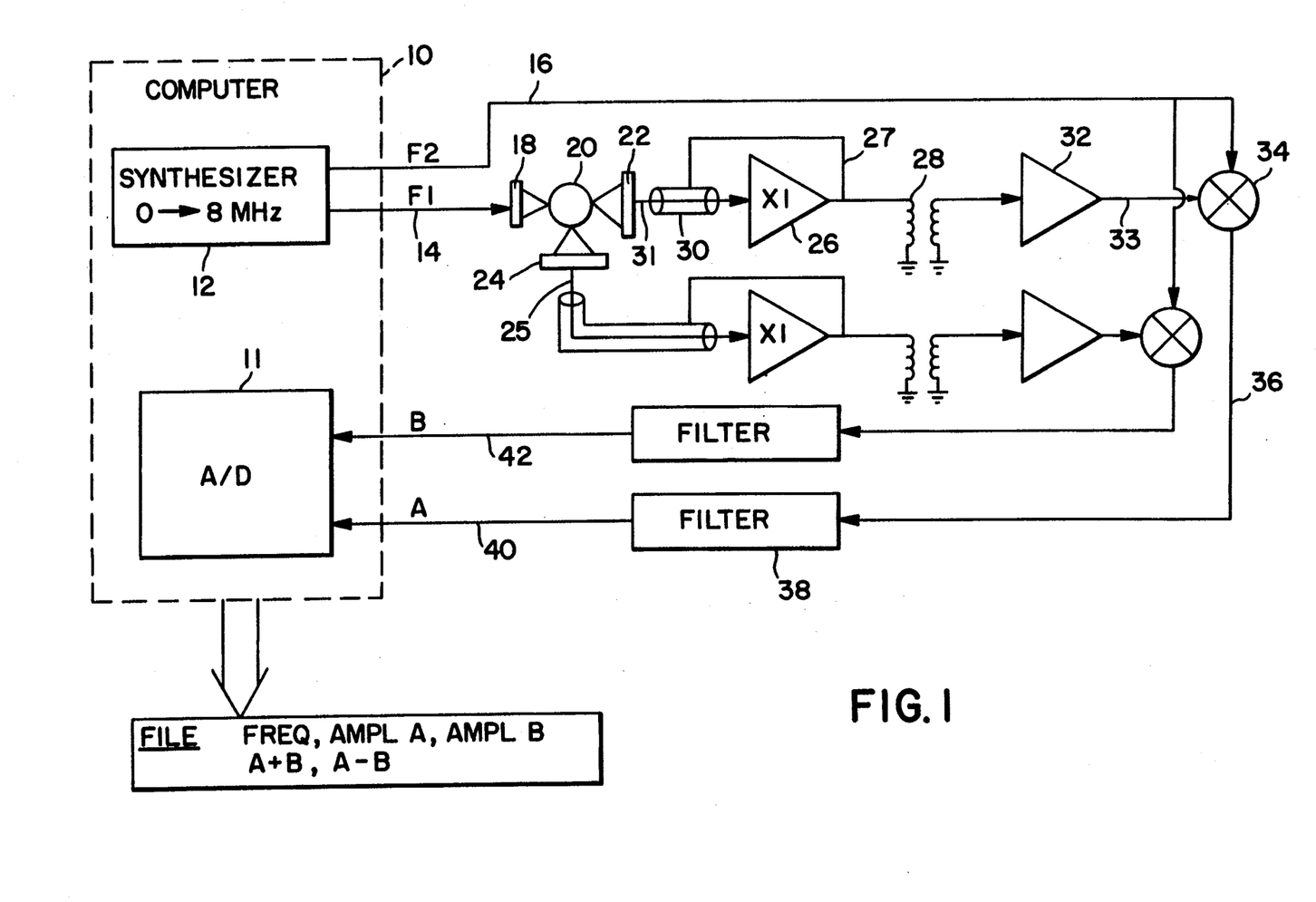
FIG. 1 shows in block-diagram form an apparatus for performing the method of the present invention.

FIG. 1 shows an apparatus for resonant ultrasound spectroscopy measurement with a plurality of sensors. Computer 10 provides for control of the synthesizer 12 and the 16 bit analog to digital converter 11 for each data input channel connected to each receiving transducer 22, 24. Transducer 22 has an output on line 31 and transducer 24 has an output on line 25.

Synthesizer 12 preferably has a frequency range from greater than 0 to 8 mHz. Synthesizer 12 provides two outputs which are the frequency F1 at output 14 and a second output which is the frequency F2 which is either F1 plus a constant frequency such as 1000 Hz for heterodyne operation of the receiver, or at F1 for homodyne operation, at line 16. A first transducer 18 is excited at a frequency F1 by synthesizer 12. Transducer 18 provides ultrasonic vibration to an object to be tested 20.

The response of the object 20 is then received by two separate output transducers 22 and 24. The circuitry from the output transducer 22 and A/D converter 11 can be identical to circuitry between transducer 24 and A/D converter 11. For this reason, only the circuitry between transducer 22 and A/D converter 11 will be discussed below. The times one (x1) amplifier 26 is connected to the transducer 22 provides current for transformer 28.

The output of transducer 22 is connected to a receiver 41 (FIG. 4), such as a Model QS-20 manufactured by Quatro Corp., although other receivers may be used. Receiver 41 is used for the purpose of providing amplification and noise rejection in the circuit between transducer 22 and A/D converter 11.

The output A (line 40) is applied to an A/D converter 11 within the computer. Typically, the A/D converter comprises a 16 bit A/D conversion for each of lines 40 and 42. The converted information is then entered into a file which consists of the measured frequency, the amplitude of A, the amplitude of B, the amplitude of A plus B, and the amplitude of A minus B. This file is then used for further analysis of the spectrum to determine characteristics of a part 20 being tested.

The computer 10 can be an IBM Personal Computer having an Intel® processor 486 operating at 33M Hertz, although other types of computers can be used.

Synthesizer 12 associated with computer 10 is a dual digital synthesizer such as Model QS-30 manufactured by Quatro corp. although other synthesizers may be used.

The times one (x1) amplifier 26 provides feedback to an inner coaxial cable shield 30 which surround the lead from transducer 22 to amplifier 26. Shield 30 is another grounded shield which can also be used for noise suppression. The outer surrounding coaxial cable is not shown in FIG. 1. If lead 31 is short, the shield 30 may be omitted because capacitance will not be too large. The purpose of the inner shield 30 is to provide a cancellation of capacitance of the connection 31.

The transformer 28 is a 4:1 step down transformer used for impedance matching to the input of amplifier 32. In this regard, it should be noted that the output impedance of amplifier 26 is much lower than the output impedance of transducer 22. This provides for the power gain and the necessary feedback to shield 30. The amplifier 32 may have a gain factor of 100:1 or a 40 db gain. The amplifier 26 is a broad-band amplifier having a band pass on the order of 50 mHz.

Figure 2:
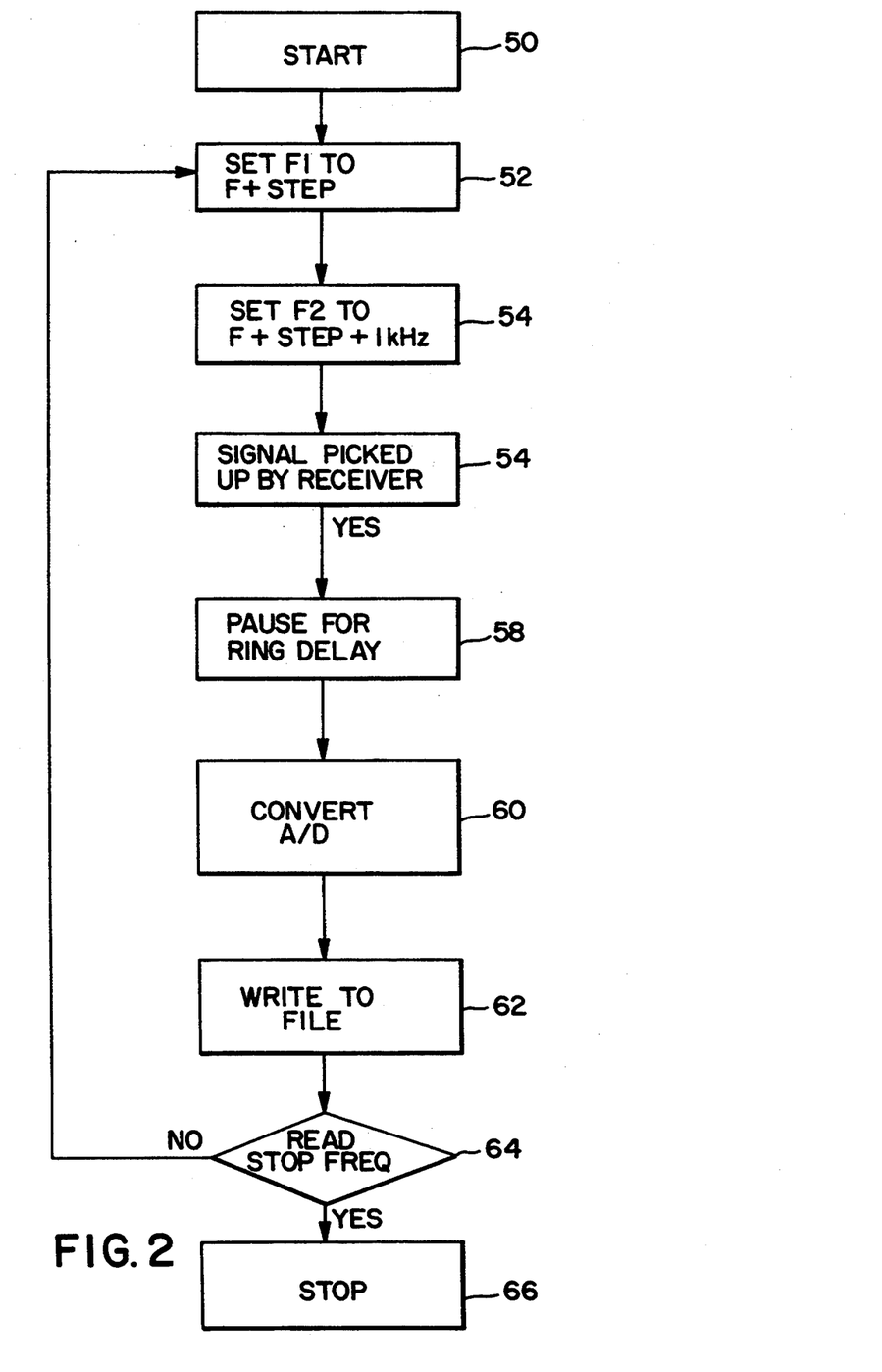
FIG. 2 shows a flow chart of the control sequence for the present invention.

Mixer 34 has an output which is a 1 kHz signal having a magnitude which is proportional to the magnitude of the frequency F-1 provided on line 14 from synthesizer 12. The function of the synthesizer is to provide a point-by-point multiplication of instantaneous values of inputs on lines 16 and 33. The mixer 34 also has many high frequency output components which are of no interest. The high frequency components are therefor filtered out by the low-band pass filter 38. Filter 38 serves to clean-up the signal from mixer 34 and provide a voltage on line 40 which is only the 1 kHz signal at an amplitude which is proportional to the amplitude of the output 31 of transducer 22. FIG. 2 is a flow diagram of the measurement steps performed by measurement of the output of either transducer 22 or transducer 24 controlled by computer 10. An initial start 50 initiates the measurement cycle, and provides initialization for the frequency F and the frequency step indicated in block 52. The frequency step may be 1 Hz or any other frequency selected for the measurement. The frequency step is determined by determining the start frequency and the stop frequency, and dividing the frequency difference by the number of steps desired for the measurement. For instance, a measurement from a start frequency of 2 kHz to a stop frequency of 3 kHz requiring 100 steps will result in a 10 Hz step.

Figure 3:
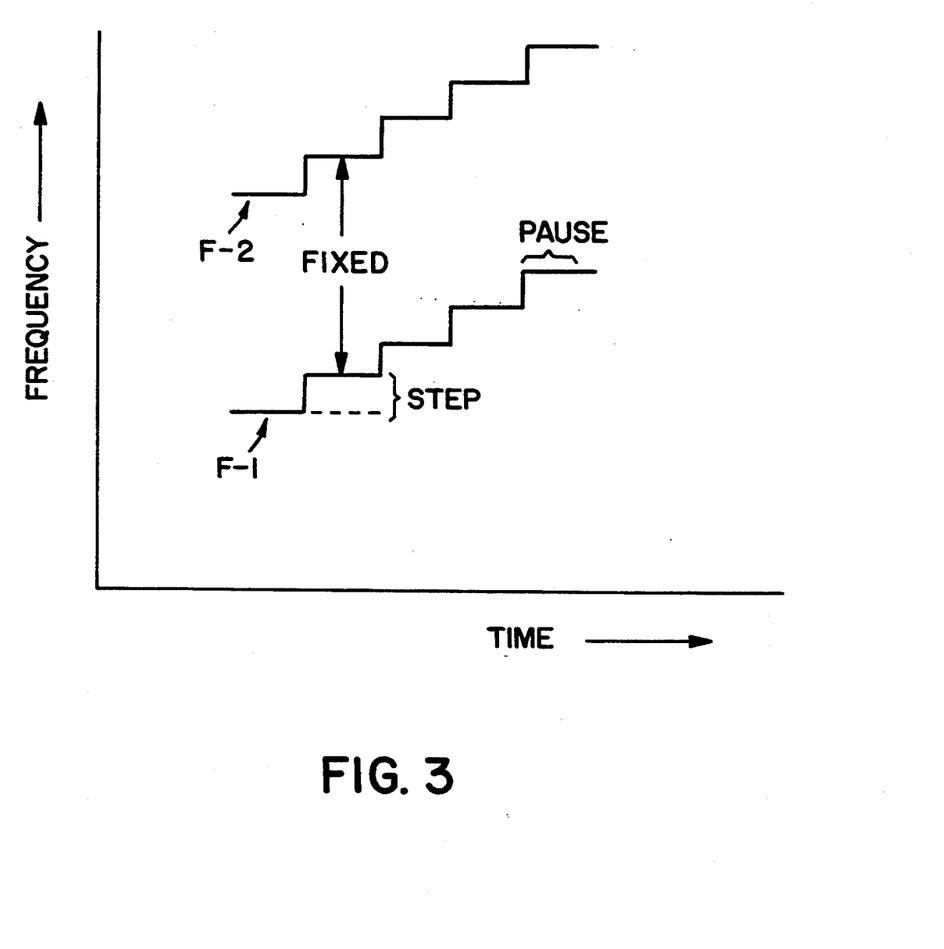
FIG. 3 shows the step-by-step increase in excitation frequency.

Once the frequency F plus step frequency is determined, the synthesizer is used to set a second frequency F2 to the value of F plus step plus 1 kHz (see block 54) if heterodyne operation is desired, or F1 if homodyne operation is desired. Homodyne may be used below 20,000 Hz, and heterodyne can be used above 1.5 kHz. In the overlap region, either may be used. In FIG. 3 the relationship between time and frequency of F1 and F2 is shown. The step is each increase in frequency, and steps are continued until the desired frequency range is traversed.

Once a signal is picked up by the receiver (i.e. an output on line 33), as indicated at 56, there is a provided a pause for ring delay as shown at block 58. The pause for ring delay is typically 30 milliseconds, although other ring delays can be used if the object under test has resonances that are narrower than a few Hz. The purpose of the pause is to give the object 20 an opportunity to reach its steady state magnitude in response to a steady input from transducer 18. The pause time is time after the frequency is applied and before detection is initiated.

After the ring delay is complete, analog-to-digital converter 11 provides an output that can be used by the data recording computer. The output of the A/D converter 11 is then written to a file by the computer as shown in block 62 for the purpose of analysis of the data by another program. Data comprising the unique signature or characterizing of the object is written into file as it is created. Once information is entered into file at step 62, subsequent processing can be used to generate a signature or characterize the object such as the resonant magnitudes, the sum of resonant magnitudes, the difference resonant magnitudes, or other manipulations of the multiple channel multiple frequency measurement which is used to perform the unique signature of the object.

Example 1

Samples of a metallic part were resonated at frequencies between 47 kHz and 51 kHz at a step width of 2.668 Hz. A separate frequency spectrum trace was prepared for each part of the type shown in FIGS. 4 and 5.

It was known that some resonances are fixed only by the dimensions while others are affected by the stiffness of the bending and torsional modes. When a crack exists, these stiffness or torsional modes become "softer" and shift to a lower frequency.

Figure 4:
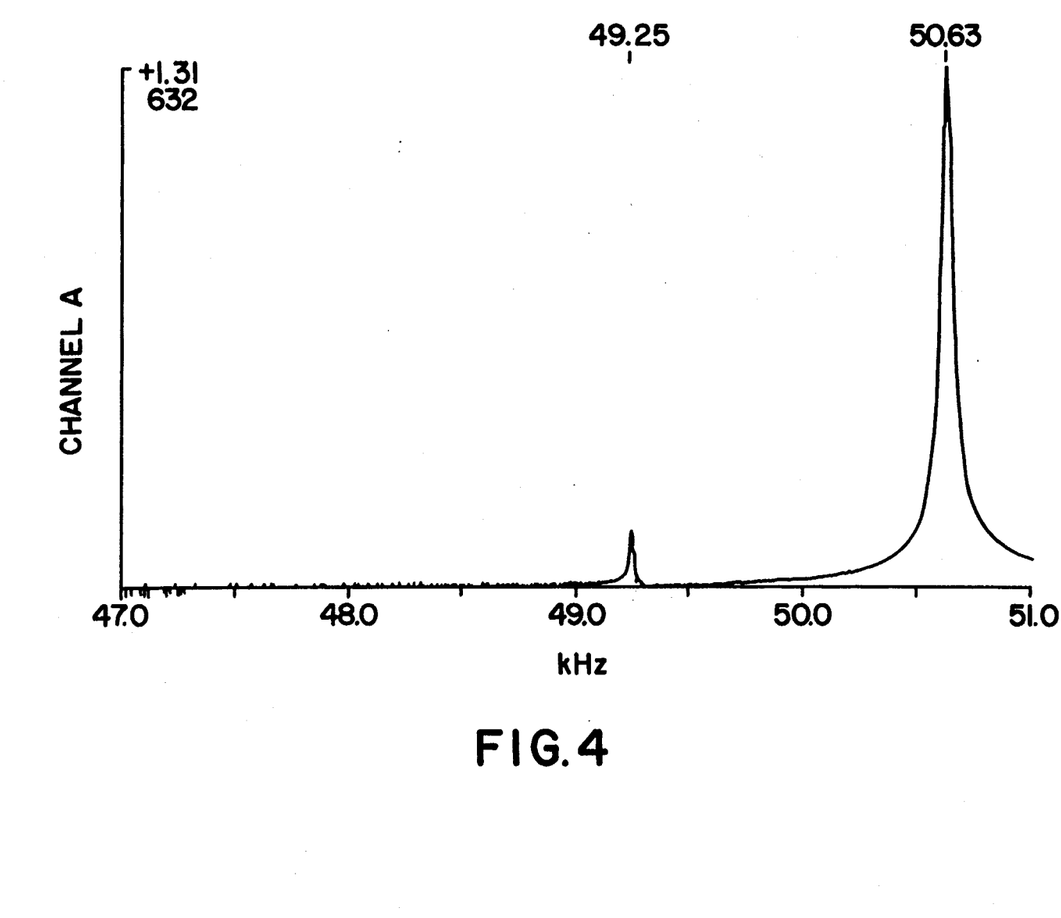
FIG. 4 shows a resonant frequency response curve of a good part.
Figure 5:
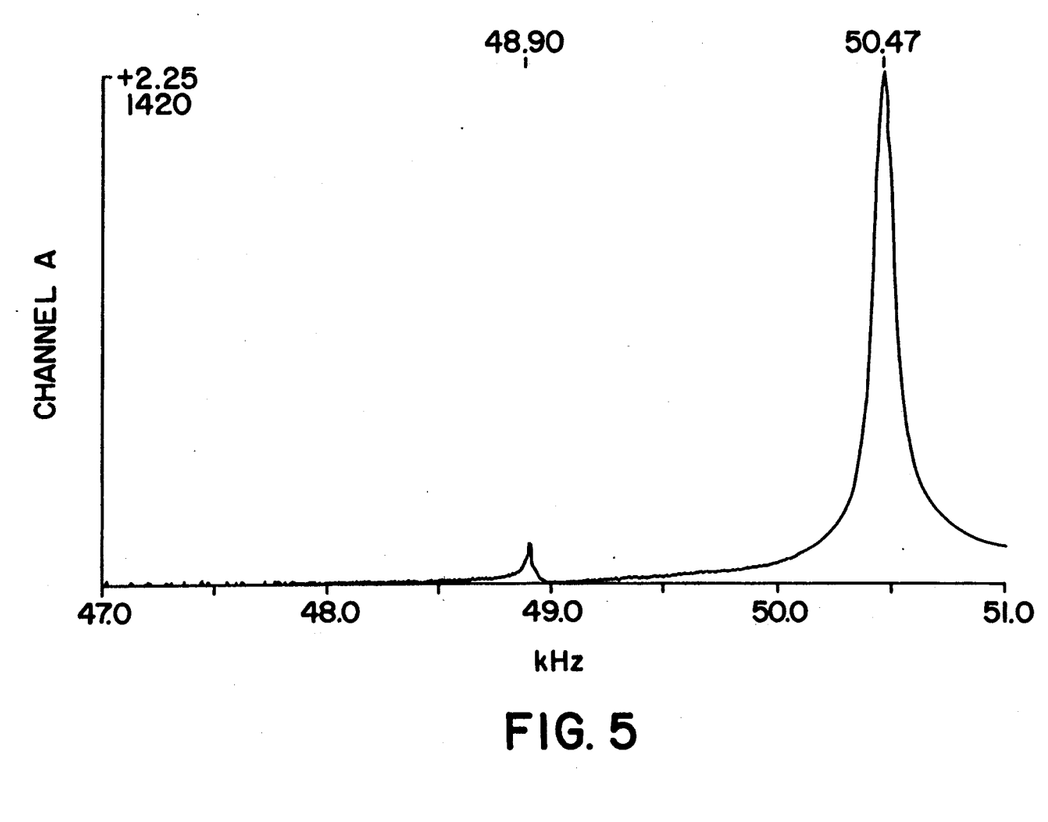
FIG. 5 shows a resonant frequency response curve of a bad part.

In this Example, a pair of resonance features between 47 and 51 kHz were located. These resonance features exhibited the desired effect in the parts under test. The 50 kHz resonance was fixed by the weight at dimensions of the part, while the mode observed at 49 kHz (approximately) appeared to rely upon the stiffness of the part. The diagnostic measurement employed was to measure the difference between these peaks and apply an arbitrary selection criteria to pass only those parts exhibiting less than a 2.75 kHz separation (see FIG. 6). A comparison of FIGS. 4 and 5 shows that the frequency of the resonant response due to the stiffness moves away from the peak due to dimension and weight. As the distance between peaks increases, the quality of the part decreases, or exhibits cracks which mostly affect the stiffness dependant resonance. FIG. 3 shows an example of a good part, and FIG. 4 shows an example of a bad part.

Figure 6:
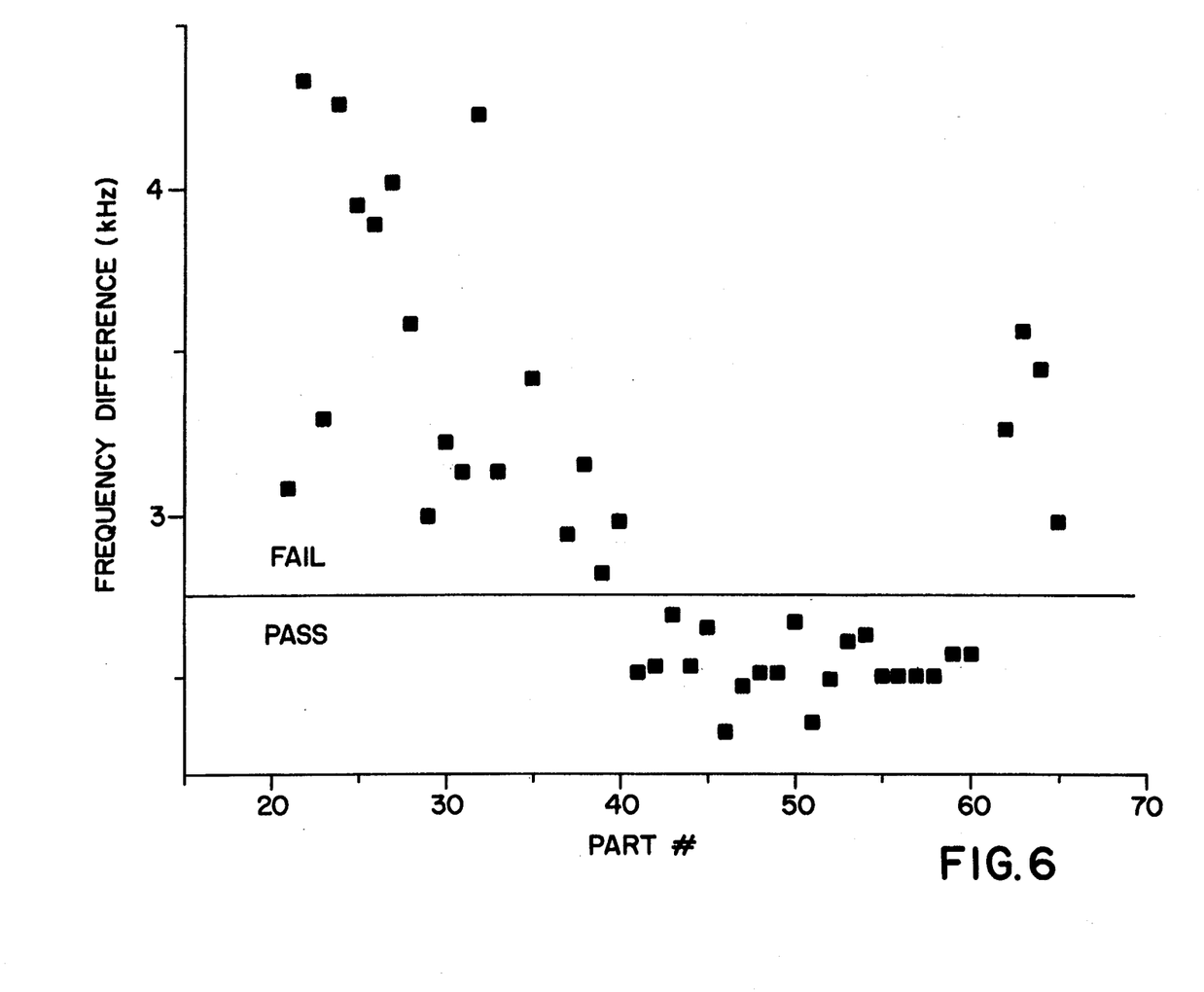
FIG. 6 shows a distribution of measurements of peak separation in percentage of a group of parts measured in accordance with Example 1.

The diagnostic measurement process was used to measure the difference between the two peaks and to apply an arbitrary selection criteria to pass only those parts exhibiting less than 2.75 kHz separation (see FIG. 6). Applicant proceeded to test 20 good parts and 26 parts with varying size cracks. The data plotted in FIG. 6 shows that parts 41–60 have peak separations which are less than 2.75 kHz while the others exhibit a greater difference. In this test, part no. 39 was previously identified as having the smallest flaw. As shown in FIG. 6, part 39 is the closest to the accept/reject criterion of 2.75 kHz.

By Applicant's technique, not only the presence of flaws is identified, but also the magnitude of the defect size can be identified through increasing percentage of shift.

The criteria for pass/fail is arbitrarily established by testing a plurality of parts which are known to be acceptable for use. This process is amenable to automation and is relatively to insensitive to the placement of the test object on the transducer fixture.

In instances where the stiffness resonance is not evident when a part was tested, the part was considered to be a fail part. All passing parts in this example exhibited both of the resonances.

Example 2

An absolute shift to lower frequencies of a stiffness mode can also be used to determine the presence of flawed parts in a population of unflawed parts. In this approach, it is not necessary to first determine a dimensional mode. Instead, the absolute frequency shift between two stiffness modes is detected and used to evaluate parts.

In this method for distinguishing between unknown flawed and unflawed parts the resonant frequency which is dependant on a particular stiffness mode of an unflawed part is first determined. Then a resonant frequency which is dependant upon stiffness of an unknown flawed part is determined. The resonant frequency of the unflawed part and the resonant frequency of the unknown flawed part is then made. The evaluation of the unknown flawed is then made based upon the magnitude of the difference between the resonant frequency of the unflawed part and the resonant frequency of the flawed part as determined by the comparator.

What is claimed is:

1. A method for determining if a part is flawed, comprising the steps of:
   detecting frequency of at least two prominent resonant responses of said part;
   measuring frequency difference between two of said prominent resonant responses; and
   comparing said measured frequency difference between two of said prominent resonances to a predetermined unflawed part frequency difference.

2. The method in accordance with claim 1, wherein said resonant responses are a function of different physical characteristics of said part.

3. The method in accordance with claim 1, wherein one resonant response used in the measured frequency difference is dependant upon dimensions of said part.

4. The method in accordance with claim 1, wherein one resonant response used in the measured frequency difference is dependant upon stiffness of said part.

5. The method in accordance with claim 1, wherein said part is rejected when said measured frequency difference is greater than a predetermined number.

6. The method in accordance with claim 1, wherein said resonant responses are determined by contacting said part with a piezoelectric vibrator which is energized at a plurality of frequencies.

7. The method in accordance with claim 1, wherein said predetermined unflawed part frequency difference is determined by testing a plurality of parts which are known to be acceptable.

8. The method in accordance with claim 1, wherein a ratio of the measured frequency difference is determined by dividing the measured frequency difference by either of said resonant response frequencies used in the measured frequency difference.

9. The method in accordance with claim 1, wherein a ratio of the measured frequency difference is determined by dividing the measured frequency difference by the average of said resonant response frequencies used in the measured frequency difference.

10. The method in accordance with claim 3, wherein the other resonant response frequency used in the measured frequency difference is dependant upon the stiffness of said part.

11. The method in accordance with claim 4, wherein said stiffness is stiffness of bending.

12. The method in accordance with claim 4, wherein said stiffness is dependant upon torsional modes.

13. The method in accordance with claim 12, wherein a plurality of frequencies are produced by sweeping frequency of vibrations applied to said part in step intervals between a high limit and a low limit frequency.

14. The method in accordance with claim 13, wherein said step intervals are all equal.

15. A method of flaw detection in one part of a plurality of otherwise identical parts comprising the steps of:
   (1) vibrating said part at a plurality of frequencies;
   (2) identifying of a first frequency at which said part resonates;
   (3) identification of a second frequency at which said part resonates;
   (4) determining the difference between said first and second frequencies;
   (5) dividing said difference by one of said first and second frequencies to obtain a number; and
   (6) comparing said number to a predetermined number to determine the presence of a flaw.

16. The method in accordance with claim 15, further comprising the step of:
   (7) evaluating said one part based upon said comparison.

17. A method of flaw detection in one part of a plurality of otherwise identical parts comprising the steps of:
   (1) identifying first and second resonant response frequencies;
   (2) determining the difference between said first and second resonant response frequencies;
   (3) dividing said difference by one of said first and second response frequencies to determine a percentage change in frequency; and
   (4) comparing said percentage change to a standard percentage change to determine the presence of a flow.

18. The method in accordance with claim 17, wherein the step of identifying first and second resonant response frequencies comprises the steps of:
   applying a plurality of vibrations to said part in step intervals; and
   identifying of resonant response frequency peaks from a plot of applied frequency versus magnitude of resonant response.

* * * * *